(12) United States Patent
Foster (10) Patent No.: US 9,592,399 B2
(45) Date of Patent: Mar. 14, 2017

(54) DEPLOYABLE MULTI-ELECTRODE LEADLESS ELECTROSTIMULATOR

(71) Applicant: Cardiac Pacemakers, Inc., St. Paul, MN (US)

(72) Inventor: Daniel J. Foster, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 224 days.

(21) Appl. No.: 14/301,673

(22) Filed: Jun. 11, 2014

(65) Prior Publication Data
US 2014/0379041 A1 Dec. 25, 2014

Related U.S. Application Data

(60) Provisional application No. 61/837,480, filed on Jun. 20, 2013.

(51) Int. Cl.
*A61N 1/372* (2006.01)
*A61N 1/375* (2006.01)
(Continued)

(52) U.S. Cl.
CPC ....... *A61N 1/3756* (2013.01); *A61N 1/37205* (2013.01); *A61N 1/362* (2013.01);
(Continued)

(58) Field of Classification Search
CPC .. A61N 1/3756; A61N 1/37205; A61N 1/362; A61N 1/3684; A61N 1/37211; A61N 1/3787; A61N 1/3962; A61N 1/3968
(Continued)

(56) References Cited

U.S. PATENT DOCUMENTS 7,303,526 B2 12/2007 Sharkey et al.
7,532,933 B2 5/2009 Hastings et al.
(Continued)

FOREIGN PATENT DOCUMENTS

WO WO-2007001482 A1 1/2007
WO WO-2012145187 A1 10/2012

*Primary Examiner* — Christopher D Koharski
*Assistant Examiner* — Michael Carey
(74) *Attorney, Agent, or Firm* — Seager, Tufte & Wickhem LLP (57) ABSTRACT

An intravascularly-deliverable electrode assembly can be used to provide electrostimulation. The electrode assembly can include an electrostimulation circuit located in a housing, two or more elongate members coupled to the housing and configured to anchor the housing to a heart, the two or more elongate members including two or more electrodes electrically coupled to the electrostimulation circuit and controllably addressable by the electrostimulation circuit for delivery of an electrostimulation to the heart. The two or more elongate members can be sized and shaped for intravascular delivery to the heart in a first configuration, and in response to a user actuation, the two or more elongate members can move to a second configuration that is expanded relative to the first configuration to securely anchor the intravascularly-deliverable electrode assembly to the heart. Circuitry within the electrode assembly can coordinate electrostimulation, such as for delivery to sites near each electrode.

20 Claims, 6 Drawing Sheets

(51) Int. Cl.
  *A61N 1/378* (2006.01)
  *A61N 1/39* (2006.01)
  *A61N 1/362* (2006.01)
  *A61N 1/368* (2006.01)

(52) U.S. Cl.
  CPC .......... *A61N 1/3684* (2013.01); *A61N 1/3787* (2013.01); *A61N 1/37211* (2013.01); *A61N 1/3962* (2013.01); *A61N 1/3968* (2013.01)

(58) Field of Classification Search
  USPC ................. 607/5, 60, 119, 126, 128; 600/37
  See application file for complete search history.

(56) References Cited

U.S. PATENT DOCUMENTS

| | | | |
|---|---|---|---|
| 7,650,186 B2 | 1/2010 | Hastings et al. | |
| 7,862,500 B2 | 1/2011 | Khairkhahan et al. | |
| 8,025,495 B2 | 9/2011 | Hardert et al. | |
| 8,043,329 B2 | 10/2011 | Khairkhahan et al. | |
| 8,204,605 B2 | 6/2012 | Hastings et al. | |
| 8,221,445 B2 | 7/2012 | van Tassel et al. | |
| 8,398,537 B2 | 3/2013 | Khairkhahan et al. | |
| 8,500,790 B2 | 8/2013 | Khairkhahan | |
| 8,500,795 B2 | 8/2013 | Khairkhahan et al. | |
| 8,657,873 B2 | 2/2014 | Khairkhahan et al. | |
| 8,672,827 B2 | 3/2014 | Nikolic et al. | |
| 8,747,454 B2 | 6/2014 | Khairkhahan et al. | |
| 9,078,660 B2 | 7/2015 | Boutillette et al. | |
| 2004/0147973 A1 | 7/2004 | Hauser et al. | |
| 2006/0030881 A1 | 2/2006 | Sharkey et al. | |
| 2008/0283066 A1 | 11/2008 | Delgado et al. | |
| 2009/0018599 A1 | 1/2009 | Hastings et al. | |
| 2011/0087066 A1* | 4/2011 | Boutillette ....... A61B 17/12022 600/37 |
| 2011/0303229 A1 | 12/2011 | Najafi et al. | |
| 2012/0291788 A1 | 11/2012 | Griswold et al. | |
| 2012/0296222 A1 | 11/2012 | Griswold et al. | |
| 2012/0330392 A1* | 12/2012 | Regnier ................. A61N 1/059 607/119 |
| 2013/0116740 A1* | 5/2013 | Bornzin ............... A61N 1/3756 607/9 |

* cited by examiner

DEPLOYABLE MULTI-ELECTRODE LEADLESS ELECTROSTIMULATOR

CLAIM OF PRIORITY

This application claims the benefit of priority under 35 U.S.C. §119(e) of Foster, U.S. Provisional Patent Application Ser. No. 61/837,480, titled "DEPLOYABLE MULTI-ELECTRODE LEADLESS ELECTROSTIMULATOR," filed on Jun. 20, 2013, which is hereby incorporated by reference herein in its entirety.

BACKGROUND

Active implantable medical devices (IMDs) can be used to treat a variety of symptoms or diseases. For example, an IMD can be used to generate therapeutic electrostimulation for delivery to one or more tissue sites, such as including one or more cardiovascular or neural targets. Such electrostimulation therapy can include one or more of a cardiac pacing therapy, a cardioversion or defibrillation therapy, a cardiac resynchronization therapy, a neural stimulation therapy that can include, for example, an autonomic modulation therapy (AMT), a neurological disorder therapy, a pain management therapy, or one or more other electrostimulation therapies.

An example of an IMD can include a battery-operated electronics unit implanted under the skin, such as in the pectoral region, electrically and mechanically connected to one or more intravascular leads extending into a heart chamber or one or more coronary blood vessels. The one or more intravascular leads can include one or more electrodes to electrostimulate the heart tissue and sense potentials at the heart tissue (e.g., for sensing intrinsic cardiac activity, or sense an evoked response to the application of electrostimulus).

However, the use of such leads can be precluded in certain circumstances, particularly in blood vessels having limited available cross sectional area, or in portions of the body such as certain heart chambers, where such leads can be contraindicated for chronic implantation due to one or more of a risk of thrombus formation or lead dislodgement.

OVERVIEW

The present inventor has recognized, among other things, that a compact intravascularly-deliverable electrode assembly can be used in a variety of locations, such as along with tethered intravascular leads or instead of using tethered intravascular leads. The intravascularly-deliverable electrode assembly, which can be "leadless," can be used in applications where electrostimulation is desired to augment or replace electrostimulation or physiologic sensing provided by a tethered intravascular or subcutaneous lead. In an example, delivery of an electrostimulation therapy can be coordinated between an intravascularly-deliverable electrode assembly and one or more other implantable devices, including other intravascularly-deliverable electrode assemblies, or a subcutaneously-located pulse-generator (PG) or implantable cardioverter defibrillator (ICD), for example. The intravascularly-deliverable electrode assembly can be sized and shaped to be securely anchored in an endocardial location, such as contained within a ventricle of a heart. The intravascularly-deliverable electrode assembly can provide other therapeutic benefits, such as being sized and shaped to provide a ventricular partitioning therapy (VPT). In an example, an intravascularly-deliverable electrode assembly can include an electrostimulation circuit located in a housing, two or more elongate members including electrodes respectively electrically coupled to the electrostimulation circuit and controllably addressable by the electrostimulation circuit for delivery of an electrostimulation using a specified combination of electrodes.

Respective elongate members can include at least one end mechanically coupled to the housing, and can be sized and shaped for intravascular delivery to a specified location within the heart when in a first configuration (e.g., a non-deployed configuration). In response to a user actuation, the respective elongate members can be configured to self-expand to provide an expanded second configuration (e.g., a deployed configuration), such as to securely anchor the intravascularly-deliverable electrode assembly at a specified location within the heart.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
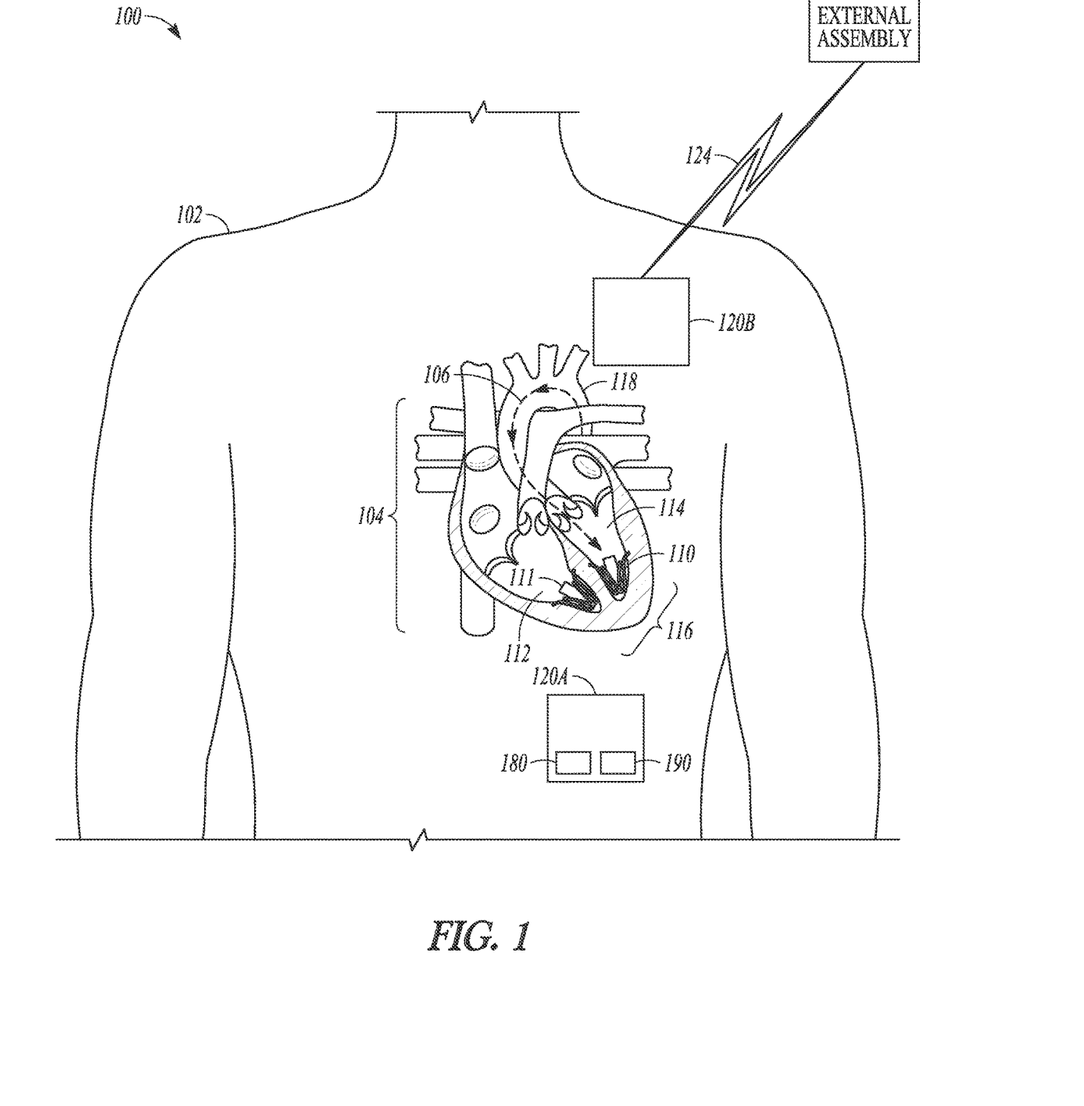
FIG. 1 illustrates generally an example of a system that can include an intravascularly-deliverable electrode assembly located within the heart.

FIG. 1 illustrates generally an example of a system 100 that can include a first intravascularly-deliverable electrode assembly 110 located within the heart 104, such as in a left ventricle 114. The system 100 can include one or more other active implantable medical devices (IMDs), such as a first IMD 120A, located subcutaneously in a location nearby the heart (e.g., a subcutaneous Implantable Cardioverter Defibrillator (ICD)), a second IMD 120B, located subcutaneously (or submuscularly, for example) in a pectoral location (e.g., a pacemaker or ICD having a tethered intravascular lead), or other IMDs located elsewhere. Other IMDs can include other electrode assemblies, such as similar to the first intravascularly-deliverable electrode assembly 110, but located elsewhere, such as a second intravascularly-deliverable electrode assembly 111 in a right ventricle 112 of the heart 104. While the example of FIG. 1 illustrates first and second intravascularly-deliverable electrode assemblies 110 and 111, such electrodes may be included stand-alone without requiring other electrode assemblies or IMDs 120A or 120B.

The first intravascularly-deliverable electrode assembly 110 can be delivered to an endocardial location using a variety of different routes, such as a transfemoral route, including a traversal 106 through the interior of the aorta 118, or through the inferior vena cava (IVC) then transseptally such as from the right atrium to the left atrium at or near the fossa ovalis. The transfemoral route can generally include obtaining access to the femoral artery percutaneously and then a traversal through the interior of the vasculature, such as using a catheter-based delivery technique.

Other approaches can include a percutaneous access of a subclavian vein or an axillary artery, for example. A similar approach can be used for delivery of other intravascularly-deliverable electrode assemblies, such as the second intravascularly-deliverable electrode assembly 111. For example, a subclavian approach can be used to gain access to the right chambers of the heart through the superior vena cava (SVC). In an illustrative example, one or more of the first intravascularly-deliverable electrode assembly 110 or the second intravascularly-deliverable electrode assembly 111 can be delivered to the endocardial location within the heart 104 such as using a delivery system shown in the examples of FIG. 2A or 2B.

The first or second intravascularly-deliverable electrode assemblies 110 or 111 can include one or more electrodes located on or included as a portion of one or more elongate members or struts, as discussed below in various illustrative examples. Such electrodes can be independently controllable, such as to allow coordination or control of therapy delivered by a respective electrode assembly 110, or coordination or control of therapy between multiple assemblies, such as the first intravascularly-deliverable electrode assembly 110, the second intravascularly-deliverable electrode assembly 111, the first IMD 120A, or a second IMD 120B.

For example, such independent control can include independent control of each individual electrode located on a respective electrode assembly 110, independent control of groups of electrodes located on a respective electrode assembly 110, or independent control of electrodes located on one electrode assembly 110 versus another.

In an example, one or more of the first or second IMDs 120A or 120B can include a sensing circuit 180, such as configured to obtain information indicative of physiologic electrical activity (e.g., cardiac electrical activity or neural activity). Such information can be used to coordinate timing of delivery of a specified electrostimulation, or to suppress or inhibit delivery of such a specified electrostimulation. In an example, one or more of the first or second IMDs 120A or 120B can include a defibrillation circuit 190. Any combination of the first and second intravascularly-deliverable electrode assemblies 110 or 111, or one or more of the first or second IMDs 120A or 120B can provide various electrostimulation modes, for example providing cardiac resynchronization therapy (CRT) pacing of ventricular locations using some or all available electrodes, or using a coordinated or timed delivery of a sequence or series of pacing pulses in order to elicit a desired physiologic response, or using one or more sites preferentially.

In an illustrative example, the second IMD 120B can include an implantable cardioverter defibrillator (ICD), such as a subcutaneously-implanted IMD 120B including the defibrillation circuit 190, but without providing cardiac pacing support, such as bradycardia or cardiac resynchronization support. Such pacing can be provided by one or more of the first or second intravascularly-deliverable electrode assemblies 110 or 111 located within a chamber of the heart. In this example, the IMD 120B can include a subcutaneous lead to deliver the defibrillation therapy without being within or, in some cases, without touching the heart.

One or more of the first or second intravascularly-deliverable electrode assemblies 110 or Ill, or the first or second IMDs 120A or 120B can include a source of operating energy, such as a primary or rechargeable battery. In addition, or alternatively, one or more of the first or second intravascularly-deliverable electrode assemblies 110 or 111, or the first or second IMDs 120A or 120B can include an energy transmitting circuit or an energy receiving circuit, such as configured to transmit or receive energy using one or more of a conductive, radiative (e.g., optical or electromagnetic), inductive, or mechanical (e.g., acoustic) scheme.

Optionally, one or more of the first or second intravascularly-deliverable electrode assemblies 110 or 111, or the first or second IMDs 120A or 120B can include an energy harvesting circuit such as can include a piezoelectric element to harvest mechanically-coupled vibration or acoustic energy for use at least in part in operating one or more of the first or second intravascularly-deliverable electrode assemblies 110 or 111, or the first or second IMDs 120A or 120B, respectively. For example, such energy transmitting or receiving capability can but need not be used for communication of information as distinguished from transmitting or receiving operating energy, a portion of which can be delivered as the specified electrostimulation.

In an example, one or more of the first or second intravascularly-deliverable electrode assemblies 110 or 111, or the first or second IMDs 120A or 120B can be configured for wireless or conductive communication (e.g., via intrabody conduction) with one another or an external assembly 122 (e.g., a physician-operated or caregiver-operated programmer). For example, the external assembly 122 can include one or more of a display or user input, such as for configuration of one or more of the first or second intravascularly-deliverable electrode assemblies 110 or 111, or the first or second IMDs 120A or 120B. In an example, such as to conserve one or more of a volume or operating energy, a multi-hop communication configuration can be used, such as using one or more respective communication couplings between respective implants for intra-body communication, and using a longer range communicative coupling (e.g., a first communicative coupling 124) for a hop between an implant, such as the second IMD 120B, and the external assembly 122. The external assembly 122 can be equipped with wired or wireless networking capability, such as for sending or receiving information such as operating configuration or physiologic information from a remotely-located server or user interface, to or from the one or more respective implants shown in the system 100.

Figure 2A:
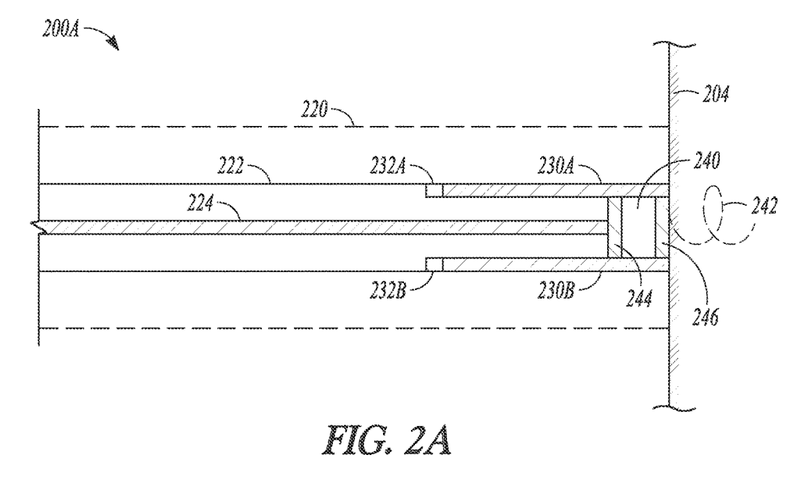
FIG. 2A illustrates generally an example that can include an intravascularly-deliverable electrode assembly in a non-deployed configuration, and a delivery system.

FIG. 2A illustrates generally an example 200A that can include a section view of an intravascularly-deliverable electrode assembly in a non-deployed configuration, and a delivery system. The delivery system can optionally include a first intravascularly-deliverable member, such as an optional guide sheath 220. The guide sheath 220 can be inserted into the vasculature and manipulated such as to position a distal end of the guide sheath 220 at or near a desired implantation location, such as at or near an interior surface of the heart 204. The delivery system can include a second intravascularly-deliverable member, such as a delivery catheter 222. If a guide sheath 220 is used, the delivery catheter can be inserted into a lumen of the guide sheath 220 so that a distal end of the delivery catheter 222 is located at or near the desired implantation location.

An intravascularly-deliverable electrode assembly can be located in a lumen of the delivery catheter 222, such as inserted within the delivery catheter 222 after position of the delivery catheter 222, or included within the delivery catheter 222 prior to intravascular insertion of the delivery catheter 222. For example, the intravascularly-deliverable electrode assembly can include a housing 240, such as can include one or more of an electrostimulation circuit, sensing circuit, or other circuits. The housing 240 can be coupled to a first elongate member 230A, such as including a first electrode 232A, or a second elongate member 230B, such as including a second electrode 232B. All electrodes need not be located along or within the respective elongate members 230A or 230B. For example, the housing 240 can include one or more electrodes, such as first housing electrode 244 or a second housing electrode 246. For example, one or more of the electrodes 232A, 232B, 244, or 246 can be independently or collectively addressable, such as assigned as a cathode or an anode for purposes of electrostimulation delivery. Other combinations or configurations of electrodes or elongate members can be included, such as shown in the examples of FIG. 1, 3-6, 7A, 7B, or 8.

The intravascularly-deliverable electrode assembly can be manipulated, such as pushed in distal direction, such as using a user-manipulated actuator 224. The actuator 224 can be coupled to the intravascularly-deliverable electrode assembly such as on a portion of the housing 240, using one or more of a threaded coupling, a friction coupling, a hook-shaped coupling, a thermal or electro-galvanically severable coupling, or using one or more other approaches.

The intravascularly-deliverable electrode assembly can, but need not, include one or more tissue-penetrating fixation elements. In an example, one or more of the actuator 224 or the delivery catheter 222 can be used such as manipulate a fixation portion 242 of the intravascularly-deliverable electrode assembly. For example, the fixation portion 242 of the intravascularly-deliverable electrode assembly can include one or more tines or a helical configuration, such as can be screwed or extended into tissue, such as extending into wall tissue of the heart 204. In an example, a cross sectional shape (e.g., hexagonal, square, or other shape) or configuration (e.g., including or more slots or other features) of the housing 244 can be engaged by the delivery catheter 222, such as to allow controllable rotation of the housing 244 in response to user actuation of the delivery catheter 222.

Figure 2B:
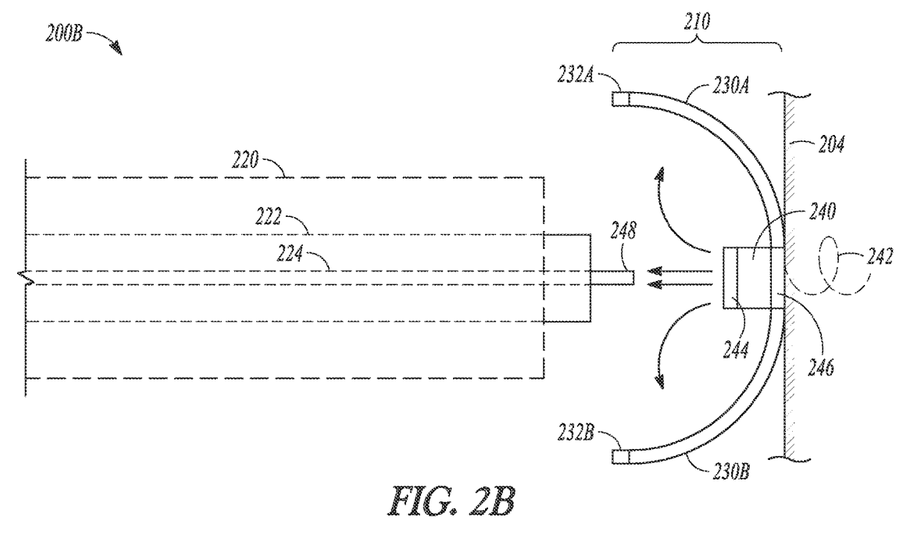
FIG. 2B illustrates generally an example that can include an intravascularly-deliverable electrode assembly in a deployed configuration, such as after retraction of the delivery system.

In FIG. 2A, the elongate members 230A or 230B can be in a first configuration (e.g., non-deployed), allowing the system to more easily traverse a body cavity such as a blood vessel, heart valve, or other region, such as during implantation. In contrast, FIG. 2B illustrates generally an example that can include an intravascularly-deliverable electrode in a deployed configuration, such as after retraction of at least a portion of the delivery system. In FIG. 2B, one or more of the optional guide sheath 220, delivery catheter 222, or actuator 224 can be retracted, such as after disconnecting a distal end 248 of the actuator 224 from the housing 240 of the intravascularly-deliverable electrode assembly.

The one or more elongate members such as the first elongate member 230A or the second elongate member 230B can self-expand, such as springing outward, such as in response to user actuation (e.g., removal) of the one or more portions of the delivery system. Such outward-springing behavior can be accomplished at least in part using a superelastic material included as a portion of the first or second elongate members 230A or 230B. For example, a superelastic material can be subjected to a deforming load or stress (e.g., such as the compression of the one or more elongate members within the delivery catheter 222 during implantation).

Upon removal (or a decrease) in stress, a superelastic material can revert (or attempt to revert when mechanically restricted) to an undeformed configuration. Such an undeformed configuration can include an "austenitic" phase, and the applied deforming load or stress can result in formation of at least some "martensitic" domains in the superelastic material. The superelastic material can exhibit a spring-like behavior where the reversion of the material to the undeformed configuration occurs as the martensitic phase domains transition to the austenitic phase. Examples of superelastic materials include certain alloys, such as a nickel-titanium alloy (e.g., "NiTi" or "Nitinol"). The housing 240 can include one or more biocompatible materials, such as titanium, stainless steel, or a biocompatible dielectric material, for example.

In an example, elongate members 230A or 230B can include a hollow configuration, such as comprising a core material that need not be superelastic, such as discussed below in the example of FIGS. 7A and 7B. Similarly, one or more of the elongate members 230A or 230B can include shapes that include tined portions or other structure protruding outward or inward with respect to a central axis of the housing 240. Such tines, along with (or instead of) an outwardly-direct self-expansion force, can provide a secure fixation or anchoring of the intravascularly-deliverable electrode assembly.

Figure 3:
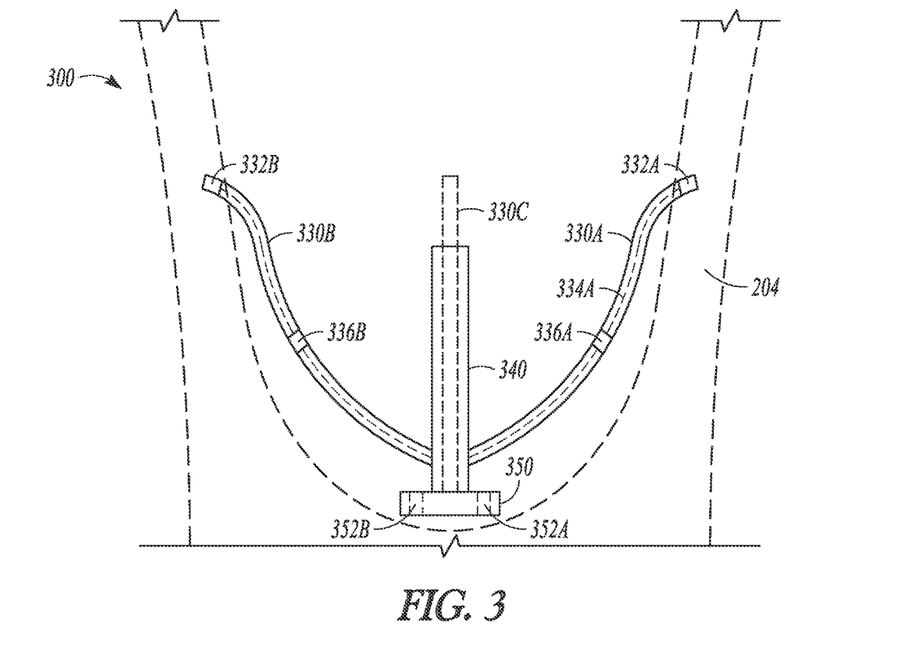
FIG. 3 illustrates generally another example of an intravascularly-deliverable electrode assembly in a deployed configuration, such as including two or more electrodes on a respective elongate member included as a portion of the electrode assembly.
Figure 4:
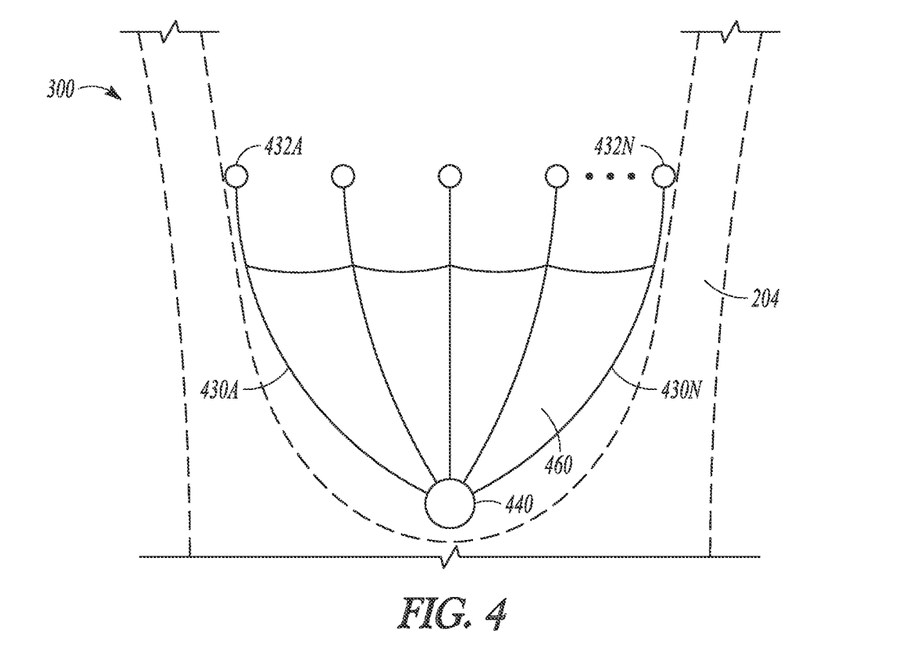
FIG. 4 illustrates generally another example of an intravascularly-deliverable electrode assembly, such as can include an umbrella-shaped or semi-hemispherical configuration, and can include membrane located between respective elongate members.
Figure 5:
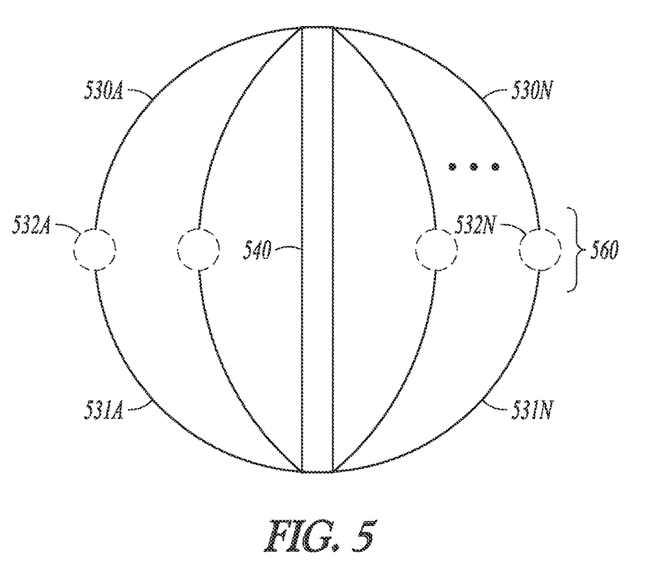
FIG. 5 illustrates generally another example that can include an intravascularly-deliverable electrode assembly, such as can have a spherical configuration when deployed.
Figure 6:
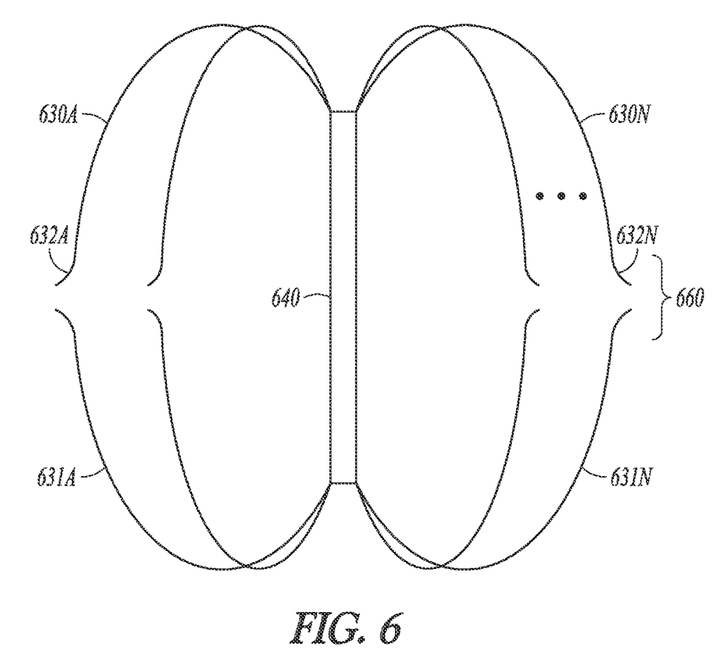
FIG. 6 illustrates generally another example of an intravascularly-deliverable electrode assembly, such as can have an elongate spherical configuration when deployed.

FIG. 3 illustrates generally another example of an intravascularly-deliverable electrode assembly 300 in a deployed configuration, such as including two or more electrodes on a respective elongate member included as a portion of the electrode assembly. In the example of FIG. 3, a housing 340 can be coupled to a base portion 350, such as including one or more hollow regions such as a first hollow region 352A or a second hollow region 352B. Such hollow regions can encourage endothelialization of the electrode assembly 300, such as when located in proximity to heart tissue 204. The housing in the example of FIG. 3 is shown as located at a proximal end of a first elongate member 330A and a second elongate member 330B, however such a housing 340 can be located elsewhere, and such elongate members 330A or 330B need not be coupled to the housing in the lateral region along the housing 340. For example, the one or more elongate members 330A or 330B can be coupled to the base portion 350, or the housing 340 can include other shapes as shown in the examples of FIG. 4 through 6 or elsewhere. While two elongate members 330A and 330B are shown in the example of FIG. 3, generally, in examples described including FIG. 3, two or more elongate members can be included such as to provide an "array" of elongate members (e.g., including a third elongate member 330C, such as coupled to the housing 340 at a radial location around the circumference of the housing 340 offset from other elongate members).

Expansion (e.g., self-expansion) of the first or second elongate members 330A or 330B can cause the elongate members to press outwards against heart tissue 204 (or against other tissue if the electrode assembly 300 is located in another body cavity elsewhere). Such an outward expansion force can help to securely anchor the electrode assembly 300, such as after a suitable implantation site has been found. The housing 340, or other portions of the electrode assembly 300, can include one or more of an electrostimulation circuit or a sensing circuit. However, the present inventor has recognized it may be difficult to position the housing 340 or other portions of the assembly in a position to obtain reliable capture of cardiac tissue during pacing therapy, or reliable sensing of cardiac electric activity.

Accordingly, the present inventor has recognized that the electrode assembly 300 can include multiple electrodes, such as one or more distal-tip electrodes (e.g., a first distal-tip electrode 332A located along the first elongate member 330A, or a second distal-tip electrode 332B located along the second elongate member 330B). Such electrodes 332A or 332B can be independently addressable, such as to provide electrostimulation (e.g., a pacing therapy) using a desired electrode configuration, such as to achieve a specified capture threshold, electrogram amplitude, or to achieve one or more other therapeutic or monitoring objectives, without requiring physical repositioning of the electrode assembly 300 (e.g., such controllability can be referred to as "electronic repositioning"). In this manner, a specified combination of one or more electrodes included as a portion of one or more elongate members can be used for delivery of electrostimulation contemporaneously using a group of electrodes, or in a sequenced manner.

To provide even more flexibility in available electrode configurations, the electrode assembly 300 can include one or more electrodes along respective elongate members, such as first mid-electrode 336A or a second mid-electrode 336B. As discussed in FIG. 7A or 7B, such electrodes can be either tied together (such as fed by a commonly-shared conductor 334A in the example of the first elongate member 330A), or using respective feed conductors. Such electrodes can be used to provide multi-site pacing at locations corresponding to each electrode. For example, a programmable offset in time between delivered electrostimulation can be provided, so that respective addressable electrodes provide respective stimulation according to a specified or programmable sequence. Alternatively, respective elongate members such as the first or second super elastic members 330A or 330B can be conductive, and can be used as respective electrostimulation or sensing electrodes without requiring a separate electrode region. In an example, one or more portions of the first or second elongate members 330A or 330B can be clad or coated with a biocompatible non-conductive material, and a "window" (e.g., aperture) can be formed in the non-conductive material to provide an exposed conductive portion forming an electrode region.

FIG. 4 illustrates generally another example of an intravascularly-deliverable electrode assembly 400, such as can include an umbrella-shaped or semi-hemispherical configuration, and can include membrane located between respective elongate members. In the example of FIG. 4, a first elongate member 430A can include one or more electrodes, such as an electrode 432A. The electrode assembly 400 can include an array of "N" elongate members, such as including elongate members 430A through 430N, and electrodes 432A through 432N. The elongate members 430A through 430N can be coupled to a housing 440, and as discussed above, the housing need not be cylindrical or located in a particular position with respect to the elongate members 430A through 430N. For example, N can equal 2, 3, 4, 5, 6, or other numbers of elongate members.

In an example, a membrane 460 can be included, such as located between or surrounding the respective elongate members 430A through 430N. For example, the membrane 460 can be sized and shaped to provide ventricular partitioning, such as when the electrode assembly 400 is delivered to an apical region of a ventricle (e.g., a left ventricle). Such a membrane can include one or more materials such as polytetrafluoroethylene (PTFE), expanded PTFE (ePTFE), Polystyrene-Polyisobutylene-Polystyrene (SIBS), e-spun SIBS, or one or more other materials such as an e-spun fluoropolymer. The membrane 460 shown in FIG. 4 can be included in other examples described herein, such as shown in FIG. 1, 2A, 2B, 3, 5-6, 7A, or 7B, for example. While the configuration shown in FIG. 4 is umbrella-shaped, other shapes can be used, and need not taper uniformly (e.g., a shell formed by the membrane 460 need not be parabolic). Also, in an example, the configuration of the electrode assembly 400 in FIG. 4 or other examples can be provided without a membrane.

In an example, one or more portions of the electrode assembly 400 can be fabricated using lithographic or printed circuit fabrication techniques. For example, the membrane can be formed (e.g., as a substrate), and one or more electrodes or other features can be deposited or attached to the substrate. The respective elongate members 430A through 430N can be formed or otherwise coupled to the substrate, such as to self-expand the membrane 460 from a first configuration (e.g., non-deployed) to a second configuration (e.g., deployed), such as in response to a user actuation.

FIG. 5 illustrates generally another example that can include an intravascularly-deliverable electrode assembly 500, such as can have a spherical configuration when deployed. In the example of FIG. 5, a housing 540 can be elongate. A first elongate member 530A can be connected to the housing at both ends, such as to form a closed path. A first electrode 532A can be located along the length of the first elongate member 530A, such as about a mid-point region 560 or elsewhere. The electrode assembly 500 can include an array of "N" elongate members, such as including respective elongate members 530A through 530N, and corresponding electrodes 532A through 532N. As in examples described elsewhere, the electrodes can be independently controllable, such as to provide electrostimulation for a pacing therapy or cardiac synchronization therapy.

For example, multiple electrodes can be included as a portion of a one or more respective elongate member 530A through 530N. As in the other examples, the respective elongate members 530A through 530N can be compressed, such as inwards toward the housing 540, in a first configuration (e.g., a non-deployed configuration), and the respective elongate members 530A through 530N can self-expand, such as when ejected from a catheter, in response to user actuation of one or more of the catheter or the electrode assembly 500. As in the examples discussed above, N can equal 2, 3, 4, 5, 6, or other numbers of elongate members.

FIG. 6 illustrates generally another example of an intravascularly-deliverable electrode assembly 600, such as can have an elongate configuration when deployed. In the example of FIG. 6, a housing 640 can be coupled to respective arrays of elongate members 630A through 630N, and 631A through 631N. When expanded (e.g., after deployment), such arrays can form two opposing basket-shaped configurations, without requiring a mechanical coupling between the respective arrays at respective distal tips of the elongate members 630A through 630N, or 631A through 631N (e.g., such as including a gap in a mid-point region 660). As in other examples, respective elongate members 630A through 630N, or 631A through 631N can include one or more features, such as respective outward-extending tined portions 632A through 632N, at respective distal tips (e.g., as shown in a distal tip region near the mid-point region 660). As in the examples discussed above, N can equal 2, 3, 4, 5, 6, or other numbers of elongate members.

One or more of the examples of FIGS. 1, 2A through 2B, or 3 through 6 can be used or combined depending on one or more of a targeted implant location, an anatomy of a particular patient or class of patients, or in view of other considerations. For example, the configuration of FIGS. 5-6 might be used in situations where ventricular portioning is not required, but where a configurable array of electrostimulation electrodes is still desired, such as within either of the ventricles of the heart.

Figure 7A:
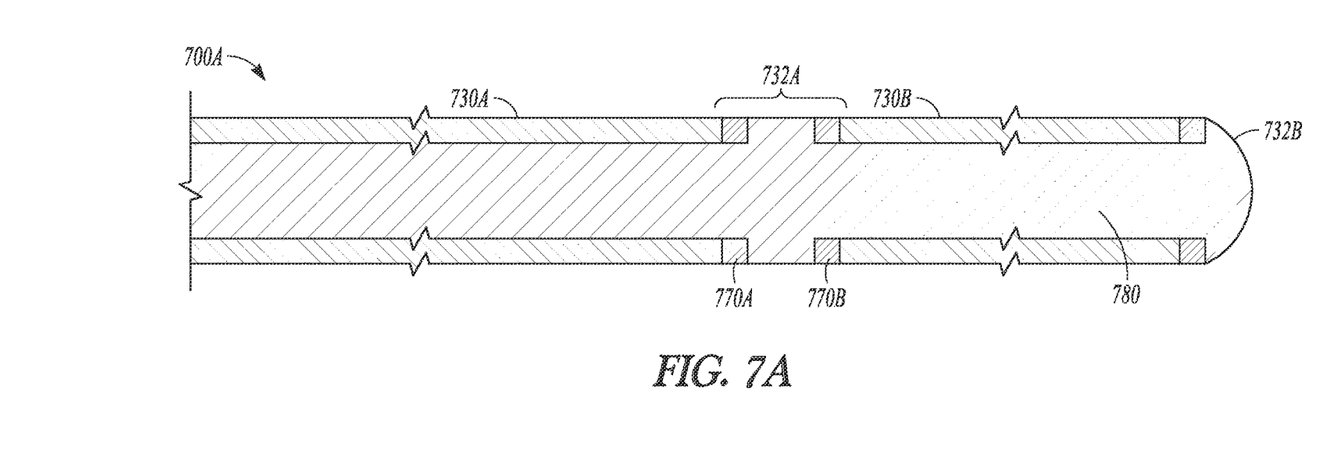
FIG. 7A illustrates generally an example of an elongate member that can be included as a portion of an intravascularly-delivery electrode assembly, such as including a hollow region.

FIG. 7A illustrates generally an example of an elongate member 700A that can be included as a portion of an intravascularly-delivery electrode assembly, such as including a hollow region 780. In the example of FIG. 7A, a first electrode region 732A and a second electrode region 732B can be connected to a commonly-shared conductor located in the hollow region 780. In an example, such a conductor can be isolated from a superelastic portion 730A of the elongate member 700A using one or more insulating portions such as a first portion 770A or a second portion 770B. In another approach, an interior of the superelastic portion 730A can be coated or clad with a non-conductive material (e.g., such as shown in the illustrative example of the insulating region 770C in FIG. 7B). While the example of FIG. 7A shows a two-electrode configuration, the elongate member 700A can include only a single electrode, or more than two electrodes.

In an example, the superelastic portion 730A can include a nickel-titanium alloy (e.g., Nitinol), such as fabricated using a drawn-filled-tube (DFT) technique. The hollow region 780 can include a core, such as silver or one or more other core materials. An electrode region, such as the second electrode region 732B can include a distal-tip electrode that is welded, swaged, crimped, or staked at the tip, such as including a platinum-iridium alloy or one or more other materials. In another example, the second electrode region 732B can be formed from material similar to, or the same as, a material comprising the hollow region 780.

Figure 7B:
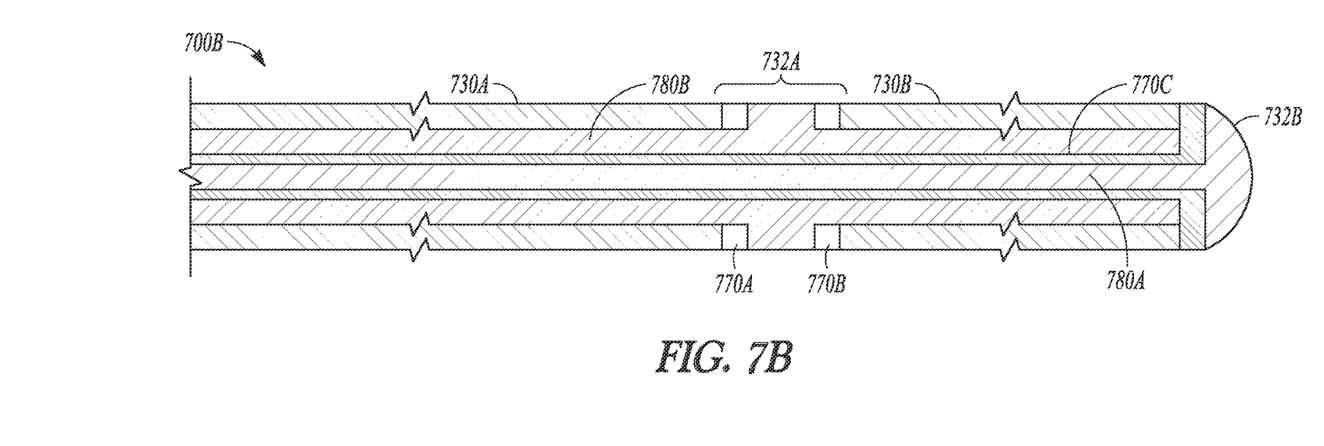
FIG. 7B illustrates generally another example of a elongate member that can be included as a portion of an intravascularly-delivery electrode assembly, such as including two independently operable electrode regions.

FIG. 7B illustrates generally another example of a elongate member that can be included as a portion of an intravascularly-delivery electrode assembly, such as including two independently operable electrode regions. In the coaxial example of FIG. 7B, the superelastic portion 730A can define an interior region. The interior region of the superelastic portion 730A can include a first conductive portion 780A (e.g., a an outer conductor), such as can be conductively coupled to a first electrode region 732A (e.g., a ring electrode), and a second conductive portion 780B (e.g., a center conductor), such as can be conductively coupled to a second electrode region 732B (e.g., a tip electrode). The second conductive region 780B can be isolated from the first conductive region 780A, such as using the insulating region 770C (e.g., a dielectric material such as PTFE, poly-ether-ether-ketone (PEEK), polyvinylidene (PVDF), or one or more other materials). Similarly to the example of FIG. 7A, the interior region of the superelastic portion 730A can be conductively isolated from the first electrode region 732A, such as using a first insulating portion 770A or a second insulating portion 770B, or one or more other configurations. In this manner, the electrode regions 730A or 730B along the elongate member 700A of FIG. 7B can be independently addressable or controllable, in contrast to the example of FIG. 7A.

While the example of FIG. 7B shows a coaxial configuration, other configurations are possible. For example, one or more conductors can be located within the interior of the superelastic portion 730A in a filar configuration rather than a coaxial configuration, or in a combination of filar or coaxial configurations. Such a filar configuration can include two or more conductors, such as respectively conductively isolated from each other, or from the superelastic portion 730A. A respective conductive portion of a respective filar can be coupled to a respective electrode region, such as the first electrode region 732A or the second electrode region 732B.

Figure 8:
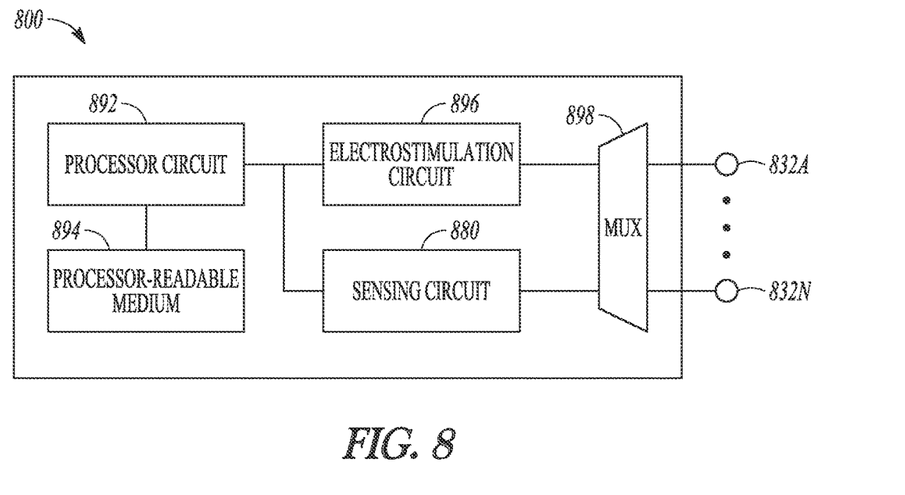
FIG. 8 illustrates generally an example of an implantable medical device (IMD), such as can include an electrostimulation circuit.

FIG. 8 illustrates generally an example of an implantable medical device (IMD) 800, such as can include an electrostimulation circuit 896. The IMD 800 can include at least a portion an intravascularly-deliverable electrode assembly, such as shown in other examples herein, or one or more other implantable assemblies. The electrostimulation circuit 896 can be coupled to one or more electrostimulation electrodes, such as any one or more of a first electrostimulation electrode 832A through an "Nth" electrostimulation electrode 832N, such as using a multiplexer (e.g., a "mux" 898) (e.g., including an electronic or mechanical switch circuit). Such electrostimulation electrodes can be located along one or more elongate members included as a portion of the IMD 800. In an example, a sensing circuit 880 can be coupled to any one or more of the first through Nth electrostimulation electrodes 832A through 832N, such as using the mux 898. One or more of the electrostimulation circuit 896 or the sensing circuit 880 can be controlled using a processor circuit 892, such as according to instructions stored using a processor-readable medium 894. The sensing circuit 880 can include one or more of an analog-to-digital converter (ADC), or other signal processing circuitry such as one or more filters or amplifiers. In an example, the sensing circuit 880 can include an amplifier having an adjustable gain, such as automatically controlled or having a user-adjustable gain.

The IMD 800 of FIG. 8 can optionally include a communication circuit, such as configured for one or more of electromagnetic (e.g., optical or radiated), mechanical (e.g., acoustic), inductive, or conductive transfer of information between the IMD 800 and one or more other implanted or external devices. For example, the communication circuit can be used for coordination of delivery of electrostimulation with a second implantable assembly separate from the IMD 800. The IMD 800 of FIG. 8 can include an energy storage element, such as one or more of a primary or rechargeable battery, or an energy harvesting element, such as configured to obtain operating energy from an environment surrounding the IMD 800.

Figure 9:
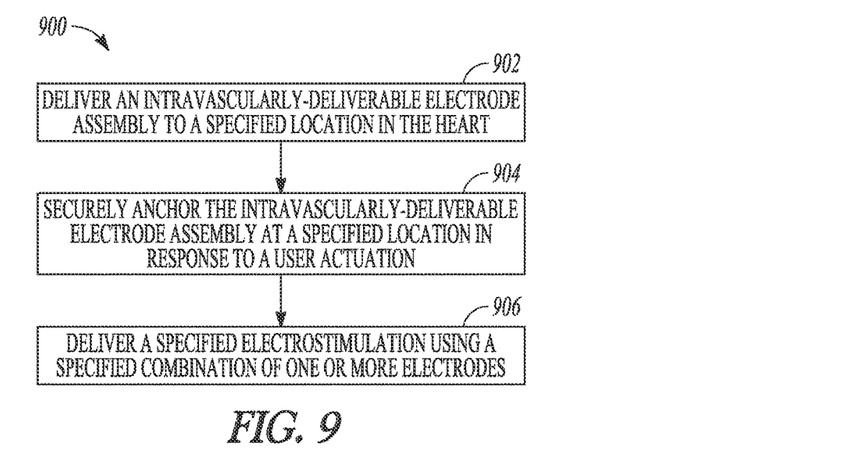
FIG. 9 illustrates generally a technique, such as a method, such as can include delivering an intravascularly-deliverable electrode assembly to a location within a heart, including one or more elongate members non-deployed first configuration, and securely anchoring the intravascularly-deliverable electrode assembly using self-expansion of the one or more elongate members.

FIG. 9 illustrates generally a technique 900, such as a method, such as can include, at 902, delivering an intravascularly-deliverable electrode assembly to a location within a heart. The intravascularly-deliverable electrode assembly can include one or more elongate members in a non-deployed first configuration, such as shown in various examples discussed above or elsewhere.

At 904, the intravascularly-deliverable electrode assembly can be securely anchored at a specified location within the heart, such as using a self-expanding behavior of the one or more elongate members. For example, the one or more elongate members can be deformed in the first configuration and can self-expand to at least attempt to revert to a non-deformed (e.g., deployed) configuration upon delivery to the specified location. At 906, an electrostimulation can be delivered using a specified combination of the one or more electrodes included as a portion of one or more of the elongate members of the intravascularly-deliverable electrode assembly.

Various Notes & Examples

Each of the non-limiting examples discussed in this document can stand on its own, or can be combined in various permutations or combinations with one or more of the other examples. The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A intravascularly-deliverable electrode assembly, comprising:
an electrostimulation circuit located in a housing; and
two or more elongate members coupled to the housing at respective fixation sites and configured to extend outward and proximally relative to the respective fixation sites to collectively anchor the housing to a heart, each of the two or more elongate members including at least one electrode such that two or more electrodes are electrically coupled to the electrostimulation circuit and controllably addressable by the electrostimulation circuit for delivery of an electrostimulation to the heart;
wherein the two or more elongate members are sized and shaped for intravascular delivery to the heart in a first configuration; and
wherein, in response to a user actuation, the two or more elongate members are configured to move to a second configuration that is expanded relative to the first configuration to securely anchor the intravascularly-deliverable electrode assembly to the heart.

2. The intravascularly-deliverable electrode assembly claim 1, wherein, in the second configuration, the two or more elongate members are configured to extend radially outward in an umbrella-shaped configuration or a spherically-shaped configuration from the one or more respective fixation sites.

3. The intravascularly-deliverable electrode assembly of claim 1, wherein, in the second configuration, the two or more elongate members are configured to provide a mechanical ventricular partitioning therapy.

4. The intravascularly-deliverable electrode assembly of claim 1, comprising a membrane located between at least two of the two or more elongate members.

5. The intravascularly-deliverable electrode assembly of claim 1, wherein at least one of the two or more elongate members includes a conductive core material coupled to at least one of the two or more electrodes.

6. The intravascularly-deliverable electrode assembly of claim 5, wherein the at least one of the two or more electrodes is positioned adjacent a distal end of the at least one of the two or more elongate members.

7. The intravascularly-deliverable electrode assembly of claim 1, wherein one of the two or more elongate members includes at least two of the two or more electrodes.

8. The intravascularly-deliverable electrode assembly of claim 7, wherein the at least two of the two or more electrodes are independently addressable by the electrostimulation circuit.

9. The intravascularly-deliverable electrode assembly of claim 1, wherein the housing includes an electrode configured for use in delivery of the electrostimulation to the heart.

10. The intravascularly-deliverable electrode assembly of claim 1, comprising a sensing circuit configured to obtain information indicative of physiologic electrical activity.

11. The intravascularly-deliverable electrode assembly claim 1, comprising an energy harvesting circuit configured to provide operating energy for the electrostimulation circuit.

12. The intravascularly-deliverable electrode assembly of claim 1, wherein the electrostimulation circuit is configured to receive or transmit information for coordination of delivery of the electrostimulation with a second implantable assembly separate from the intravascularly-deliverable electrode assembly.

13. The intravascularly-deliverable electrode assembly of claim 12, wherein the second implantable assembly is located subcutaneously.

14. The intravascularly-deliverable electrode assembly of claim 12, wherein the second implantable assembly comprises an implantable cardioverter defibrillator (ICD).

15. The intravascularly-deliverable electrode assembly of claim 1, wherein at least one of the elongate members, in response to a user actuation, is configured to self-expand to provide the expanded second configuration.

16. The intravascularly-deliverable electrode assembly of claim 1, wherein at least one of the elongate members comprises a superelastic material.

17. A system, comprising:
  an intravascularly-deliverable electrode assembly, including:
    an electrostimulation circuit located in a housing;
    two or more elongate members coupled to the housing at respective fixation sites and configured to extend outward and proximally relative to the respective fixation sites to collectively anchor the housing to a heart, the two or more elongate members each including at least one electrode such that two or more electrodes are electrically coupled to the electrostimulation circuit and controllably addressable by the electrostimulation circuit for delivery of an electrostimulation to the heart; and
    a webbing material located between at least two elongate members;
    wherein the two or more elongate members are sized and shaped for intravascular delivery to the heart in a first configuration; and
    wherein, in response to a user actuation, the two or more elongate members are configured to move to a second configuration that is expanded relative to the first configuration to securely anchor the intravascularly-deliverable electrode assembly to the heart wherein the self-expansion of the respective elongate members is limited by the webbing material; and
  a second implantable assembly configured to receive or transmit information for coordination of delivery of the electrostimulation with the intravascularly-deliverable electrode assembly.

18. The system of claim 17, wherein, in the expanded second configuration, the array is configured to extend radially outward in an umbrella-shaped configuration or a spherically-shaped configuration from respective fixation sites where respective ends of respective elongate members are mechanically coupled to the housing.

19. The system of claim 17, wherein the second implantable assembly includes one or more of an implantable pacemaker or an implantable cardioverter defibrillator (ICD).

20. A method, comprising:
  delivering an intravascularly-deliverable electrode assembly to a specified location in a heart, the intravascularly-deliverable electrode assembly including:
    an electrostimulation circuit located in a housing; and
    two or more elongate members coupled to the housing at respective fixation sites and configured to extend outward and proximally relative to the respective fixation sites to collectively anchor the housing to a heart, the two or more elongate members including two or more electrodes electrically coupled to the electrostimulation circuit and controllably addressable by the electrostimulation circuit for delivery of an electrostimulation to the heart;
    wherein the two or more elongate members are sized and shaped for intravascular delivery to the heart in a first configuration;
  in response to a user actuation, moving the two or more elongated members to a second configuration that is expanded relative to the first configuration to securely anchoring the intravascularly deliverable electrode assembly to the heart; and
  delivering a specified electrostimulation using at least one of the two or more electrodes.

* * * * *